United States Patent [19] … [11] Patent Number: 4,898,585
Borsanyi et al. … [45] Date of Patent: Feb. 6, 1990

[54] IMPLANTABLE PATIENT-ACTIVATED FLUID DELIVERY DEVICE WITH BOLUS INJECTION PORT

[75] Inventors: Alexander S. Borsanyi, Newport Beach; Michael L. Jones, Huntington Beach, both of Calif.

[73] Assignee: Baxter Healthcare Corporation, Deerfield, Ill.

[21] Appl. No.: 195,769

[22] Filed: May 18, 1988

[51] Int. Cl.$^4$ .............................................. A61M 1/00
[52] U.S. Cl. ................................................... 604/153
[58] Field of Search ..................................... 604/8–10, 604/93, 116, 131, 151, 153, 175, 181–183, 185–186, 244, 249, 246, 247, 891.1, 31, 33; 137/843, 859

[56] References Cited

U.S. PATENT DOCUMENTS

| | | |
|---|---|---|
| 3,769,982 | 11/1973 | Schulte . |
| 3,827,439 | 8/1974 | Schulte . |
| 4,013,074 | 3/1977 | Siposs . |
| 4,190,040 | 2/1980 | Schulte . |
| 4,193,397 | 3/1980 | Tucker et al. ......................... 604/93 |
| 4,258,711 | 3/1981 | Tucker . |
| 4,265,241 | 5/1981 | Portner . |
| 4,360,019 | 11/1982 | Portner . |
| 4,400,169 | 8/1983 | Stephen . |
| 4,437,457 | 3/1984 | Trick . |
| 4,487,603 | 12/1984 | Harris . |
| 4,496,343 | 1/1985 | Prosl et al. ........................... 604/131 |
| 4,511,355 | 4/1985 | Franetzki . |
| 4,543,088 | 9/1985 | Bootman . |
| 4,544,371 | 10/1985 | Dormandy . |
| 4,548,607 | 10/1985 | Harris . |
| 4,557,722 | 12/1985 | Harris . |
| 4,560,375 | 12/1985 | Schulte . |
| 4,572,168 | 2/1986 | Fischell . |
| 4,588,394 | 5/1986 | Schulte . |
| 4,594,058 | 6/1986 | Fischell . |
| 4,604,090 | 8/1986 | Reinicke . |
| 4,626,244 | 12/1986 | Reinicke . |
| 4,627,832 | 12/1986 | Hooven . |
| 4,634,427 | 1/1987 | Hammula . |
| 4,639,244 | 1/1987 | Rizk . |
| 4,655,765 | 4/1987 | Swift ................................. 604/891.1 |
| 4,666,429 | 5/1987 | Stone ................................... 604/247 |
| 4,668,231 | 5/1987 | deVries et al. ................... 604/891.1 |
| 4,692,146 | 9/1987 | Hilger ................................. 604/175 |
| 4,710,177 | 12/1987 | Smith et al. ....................... 604/153 |
| 4,781,674 | 11/1988 | Redmond et al. ..................... 604/9 |
| 4,781,680 | 11/1988 | Redmond et al. .................... 604/93 |

Primary Examiner—C. Fred Rosenbaum
Attorney, Agent, or Firm—Tilton, Fallon, Lungmus

[57] ABSTRACT

An implantable fluid delivery device for dispensing metered amounts of liquid medication when a pump assembly within its casing is operated by finger pressure applied to a central target zone of the casing's top wall. The top wall also includes an injection site spaced from the central target zone for use when a bolus of medicament is to be injected into the device and delivered directly to the patient without passing through the pump assembly. The flattened pear shape of the casing and the location of the sites for pump activation and refilling on one hand, and for bolus injection on the other, facilitate errorfree use and operation of the device. Although limited fluid backup may occur during bolus injection, a valve arrangement within the device prevents intermixing of the bolus medicament with the liquid medication in the reservoir. In a second embodiment, a supporting grid prevents possible injury to the backup-restraining valve during bolus injection.

2 Claims, 3 Drawing Sheets

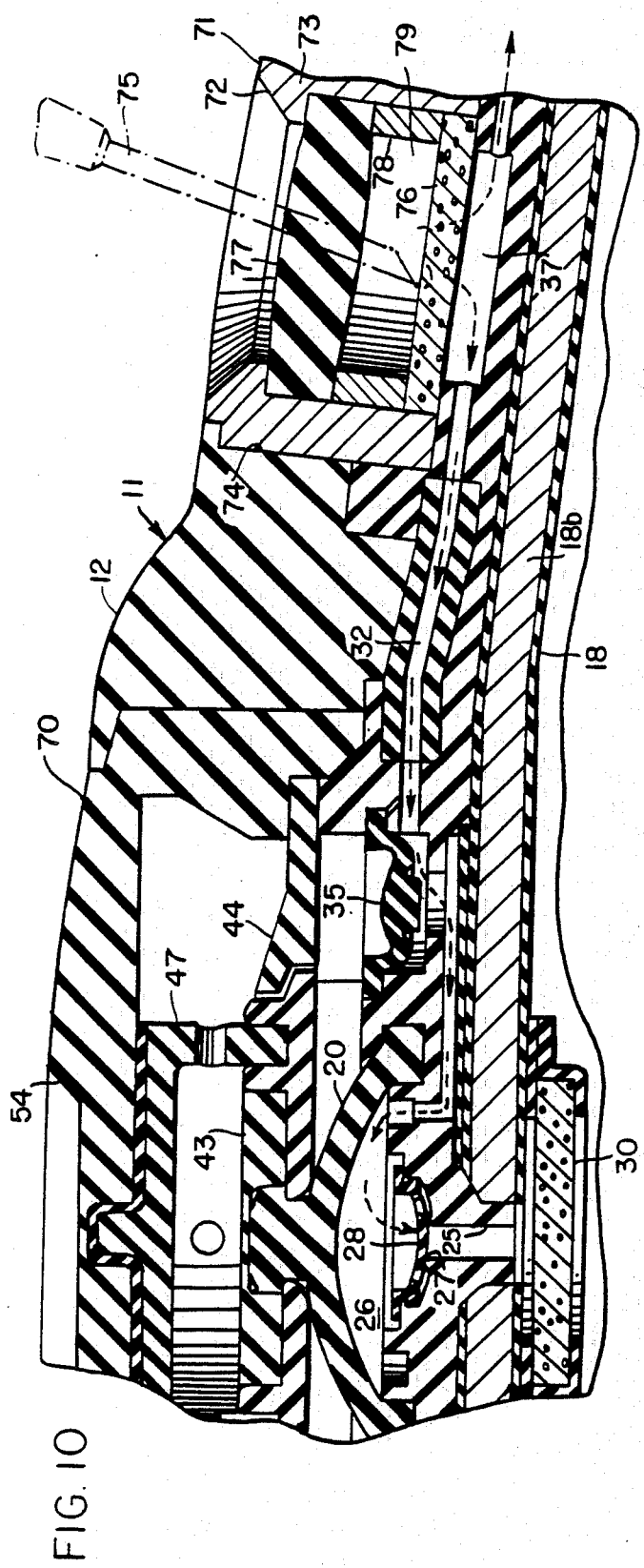
FIG. 10
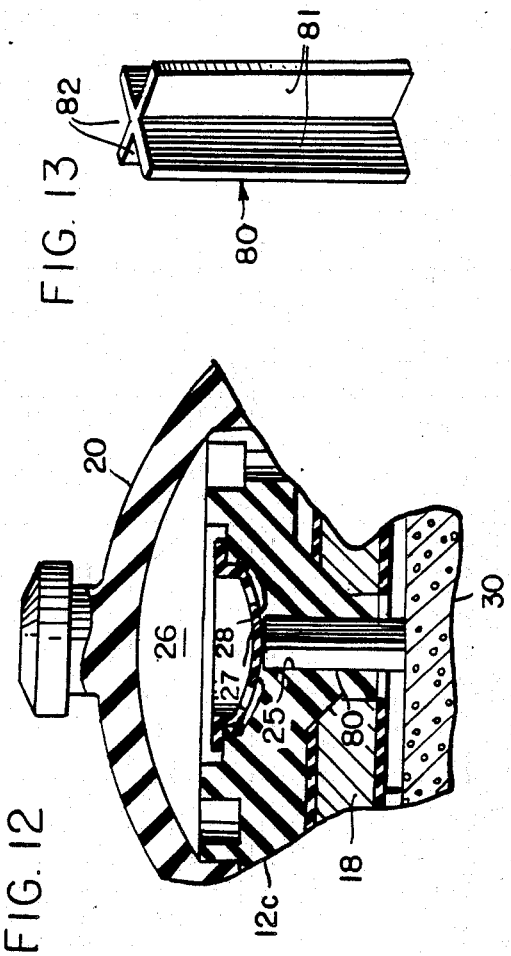
FIG. 13
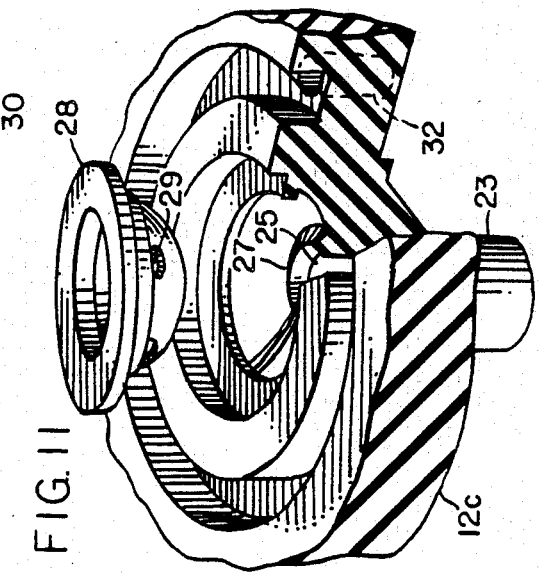
FIG. 12
FIG. 11

IMPLANTABLE PATIENT-ACTIVATED FLUID DELIVERY DEVICE WITH BOLUS INJECTION PORT

BACKGROUND OF THE INVENTION

Various implantable devices have been disclosed in the prior art that may be activated by ambulatory patients when the administration of measured doses of therapeutic agents is required. For example, cancer patients suffering from terminal lower torso cancer may require routine injections of morphine, either epidurally or intrathecally, and, upon receiving such injections, are sufficiently relieved of the symptoms of pain to move about and perform many routine and normal functions. Other chronic ailments also require frequent dosages of therapeutic agents in the treatment of chronic conditions, such as insulin in the case of diabetes. Implantable devices capable of delivering measured amounts of medicament on demand are disclosed in U.S. Pat. Nos. 4,634,427, 4,548,607, 4,588,394, 4,557,722, 4,544,371, and 4,543,088. Other U.S. patents of general interest pertaining to implantable pumping or infusing systems are 4,560,375, 4,258,711, 3,769,982, 3,827,439, 4,013,074, 4,265,241, 4,360,019, 4,487,603, 4,496,343, 4,511,355, 4,604,090, and 4,627,832. Reference may also be had to U.S. Statutory Invention Registration H150.

SUMMARY OF THE INVENTION

Despite the attention that has been directed in recent years to the development of implantable drug delivery systems, prior devices have often been deficient in significant respects. The recognition of such deficiencies is considered to be one of the important aspects of this invention, along with the discovery and development of the means for overcoming those shortcomings. Unlike many of the prior devices, the fluid delivery device of this invention is formed of soft and deformable (preferably elastomeric) material capable of being worn comfortably and effectively in implanted condition over an extended period. In spite of its compliant outer casing, the device has a relatively rigid internal structure that serves to support various operative elements, such support also performing the functions of distributing pumping forces produced by finger pressure and protecting the casing (as well as interior elements) against damage and possible leakage during refilling operations.

The compactness of the device and its ease of operation result partly from the fact that its top wall has a central target zone that may be easily located by touch (even when the device is implanted) and that serves as both the pump-actuating site against which finger pressure is exerted when drug delivery is needed and as the site for medicament injection when refilling of the reservoir is required. Enhanced self-sealing properties of the top wall and its underlying structure, coupled with a relatively rigid protective shield interposed between the top wall and the pump assembly, helps insure that the device may be easily refilled without risk of internal damage or leakage.

Even though the soft, resilient casing of the device yields or deforms with body movements and in response to both internally and externally applied forces, fluid pressure equalization within the device insures that pump activation and drug delivery do not occur unless directed and localized force is applied specifically to the target zone—a force that can be expected to be applied only intentionally.

The target zone for actuating and refilling the device is centrally disposed in an enlarged portion of the casing of generally circular outline when viewed in plan. A reduced integral portion of the same casing provides a bolus injection site spaced laterally from the main site for pump activation and reservoir replenishment. Because of the reduced dimensions of the casing portion that provides the bolus injection site, and because of the generally distinctive configuration of the casing as a whole, a physician or nurse, through tactile inspection, may easily determine the location of the bolus injection site of an implanted device and, by injecting into that site, supply a dose of selected medicament (which may be the same agent, or a different agent, than the one contained in the device's reservoir) to the patient. The bolus injection site is self-sealing and is constructed so that intermixing of the injected agent with the fluid in the reservoir of the device is prevented. Such prevention occurs not only because of protective barriers that limit needle penetration but also because of secondary functions performed by the check valve system of the device. In addition, because of the lateral relationship between the bolus injection site and the combination filling/pump-acivating site, a unitary implantable device of relatively low profile is provided.

In brief, the implantable fluid delivery device includes a casing formed of soft, deformable polymeric material, preferably elastomeric material, having top and bottom walls defining a fluid reservoir therebetween. A rigid support plate is disposed within the casing and divides the reservoir into upper and lower chambers that communicate with each other through an opening in the plate. Compressible pumping means is mounted upon the plate within the upper chamber and includes a deformable pump housing that defines a pump cavity with a first passage connecting that cavity with the lower chamber of the reservoir. A second passage connects the same cavity with the outlet port of the device, and check valves are positioned to control flow through the respective passages.

The top wall of the casing includes a flexible pump-actuating zone. Connecting means in the form of a self-sealing septum combined with a rigid cover plate operatively connect the top wall's pump actuating zone with the pump housing. The self-sealing properties of the piercable septum are enhanced by a construction that maintains that septum in a partially-compressed state. Although the casing and many of the components contained within it are readily deformable, being formed of silicone rubber or other suitable material, and although build up of fluid pressure due to unexpected compressive loads on the device is possible, pressure equalization within the reservoir, on opposite sides of elements such as the deformable pump housing and the check valve for the second passage, insure that deformation of the casing will not result in fluid delivery unless such deformation specifically includes depression of the target zone of the top wall in the direction of the compressible pump.

A porous metal filter is mounted upon the support plate at the entry to the first passage leading from the reservoir to the pump cavity. In addition to filtering fluid, the filter also performs a rate controlling function and therefore prevents surges of fluid, produced by compressive deformation of the device's deformable casing, that might otherwise cause damage to the pump assembly. Channel-defining ribs within the reservoir also function to equalize pressure within that reservoir and prevent obstructive contact with the rigid filter that might block fluid flow to the pump cavity. The bolus injection site also includes a self-sealing septum or membrane maintained in a compressed state and associated with a rigid metal filter, similar to the first filter, that limits needle penetration and throttles the rate of fluid flow at the bolus injection site.

Other features, objects, and advantages will become apparent from the specification and drawings.

DRAWINGS

FIG. 10 is an enlarged longitudinal sectional view illustrating the relationship between the bolus injection site, outlet valve, and inlet valve at the time of bolus injection.

FIG. 11 is an enlarged perspective view of the inlet valve member and its valve seat.

FIG. 12 is an enlarged vertical sectional view of a modified construction including a supportive grid for the inlet valve member.

FIG. 13 is a perspective view of the grid insert of the embodiment of FIG. 12.

DETAILED DESCRIPTION OF PREFERRED EMBODIMENT

Figure 1:
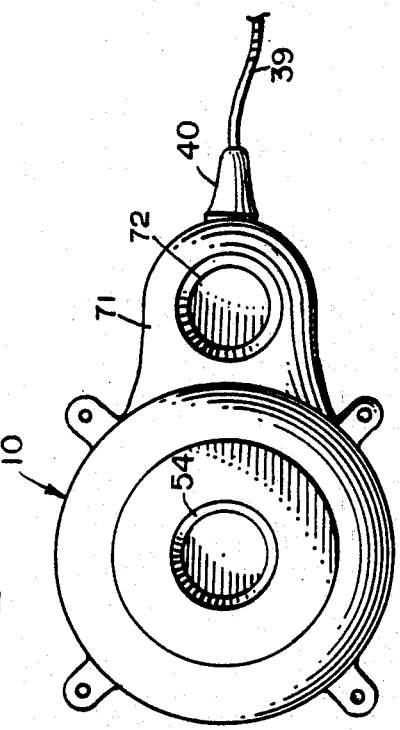
FIG. 1 is a perspective view of an implantable fluid delivery device embodying this invention.
Figure 2:
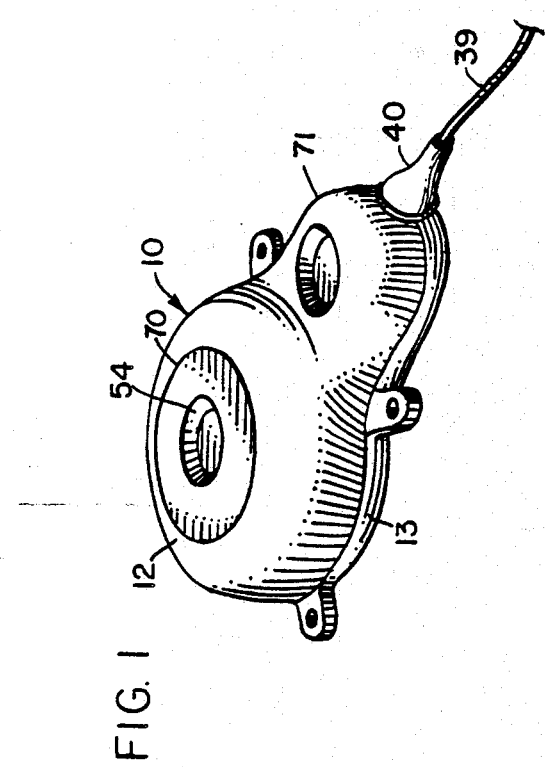
FIG. 2 is a top plan view.
Figure 3:
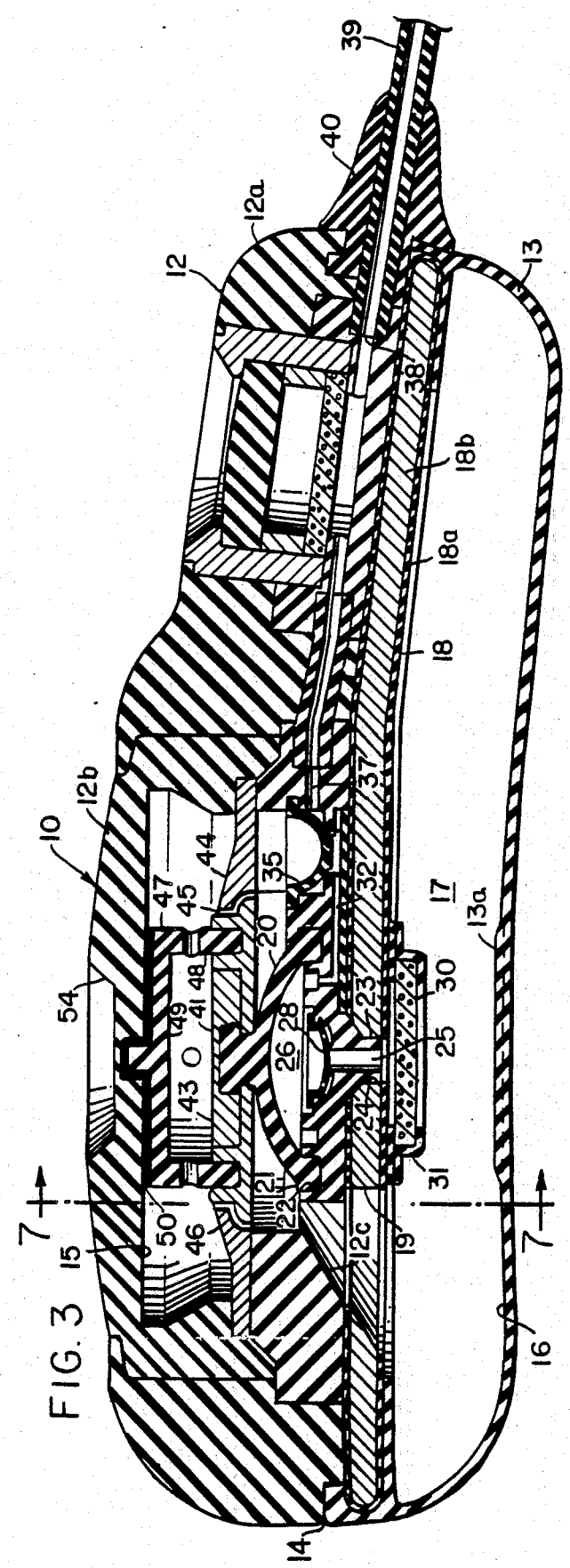
FIG. 3 is an enlarged longitudinal vertical sectional view of the device.

Referring to the drawings, and particularly to FIGS. 1-3, the numeral 10 generally designates an implantable delivery device having a casing 11 formed of soft, deformable polymeric material. While various materials having such properties might be used, an elastomeric material such as silicone rubber has been found particularly effective because of its deformability, recoverability, durability, and biocompatability. Viewed generally, the casing includes preformed (molded) upper and lower walls 12 and 13 that are sealed together along a horizontal midline 14. To facilitate manufacture, the upper wall 12 may be formed in two or more sections that allow the prefabrication of subassemblies. Thus, in the illustration given, upper wall 12 includes main section 12a central section 12b and inner section 12c. The central and inner sections together define an upper chamber 15, whereas the bottom wall defines a lower chamber 16. The two chambers communicate and together define an enlarged reservoir 17.

Figure 7:
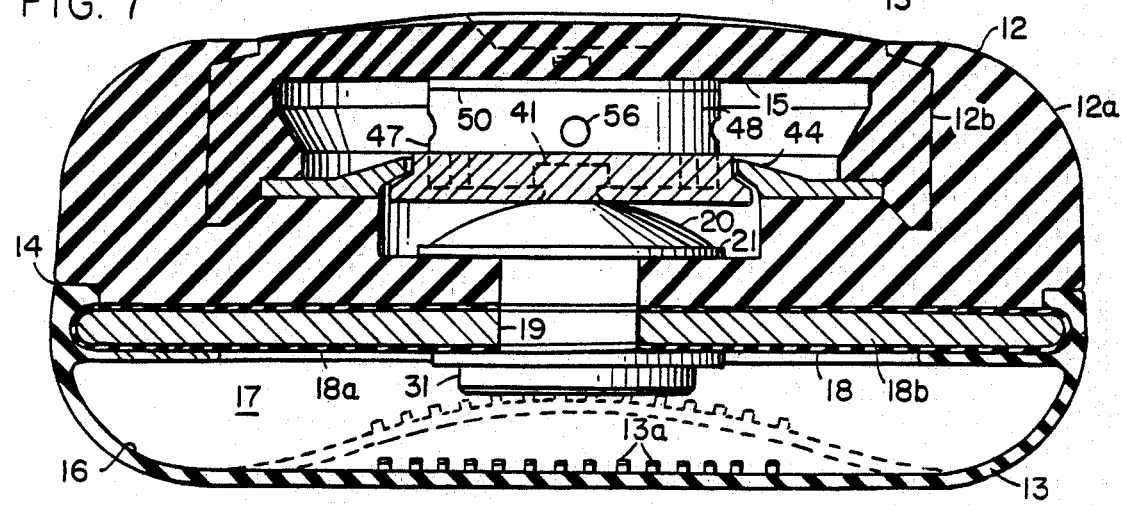
FIG. 7 is a transverse sectional view taken along line 7—7 of FIG. 3.

A relatively rigid support plate 18 is interposed between the upper and lower chambers of the reservoir and, as shown most clearly in FIGS. 3 and 7, extends substantially the full width and length of the casing. The plate is sandwiched between the upper and lower walls 12 and 13 and, if desired, may be provided with an outer layer 18a of silicone rubber or other suitable material to enhance biocompatability and facilitate adhesive attachment of the parts. The core 18b of the support plate may be formed of any tough and rigid material, including metallic and ceramic materials, although a polymeric material such as polycarbonate is believed particularly suitable. Opening 19 through the support plate 18 places the upper and lower chambers 15, 16 of the reservoir in communication with each other. In use of the device, at least the lower chamber of the reservoir would contain a liquid medicament to be discharged in metered amounts upon actuation of the device; however, for clarity of illustration such fluid is not depicted in the drawings.

The pumping means for the device is located in the upper chamber 15 of the reservoir and is supported upon plate 18. The pumping means includes a dome-shaped pump housing 20 formed of silicone rubber or other suitable elastomeric material. The rim 21 of the pump housing is secured within an annular channel 22 provided in the upper surface of inner wall section 12c, and a downwardly-projecting stem portion 23 of that wall section projects through an opening 24 in the rigid support plate. Inlet flow passage 25 extends through the stem portion 23 and places the pump chamber or cavity 26 in communication with the lower chamber 16 of the reservoir. An annular valve seat 27 is provided at the upper end of passage 25 and is normally engaged by a dish-shaped elastomeric membrane valve member 28 that has its circular outer peripheral portion secured to wall section 12c. Like other components of the drug delivery device, the membrane valve member 27 may be formed of silicone rubber. As shown most clearly in FIGS. 4-6, the valve member is provided with openings 29 therethrough that are located outboard of valve seat 27 and that therefore allow flow of fluid between passage 25 and pump chamber 26 only when the valve member 28 is urged away from valve seat 27.

Directly below the pump, and mounted along the underside of the support plate 18, is a rigid filter member or disc 30. The disc may be formed of sintered metal or a fine metallic mesh and is secured in place by an annular rim 31 adhesively bonded to the underside of the support plate 18 about the entrance to inlet passage 25. Directly below the filter disc 30, the surface of the bottom wall of the casing is provided with parallel ribs 13a that prevent the bottom wall from blocking fluid flow from lower chamber 16 into filter 30 and inlet passage 25 should the bottom wall be flexed upwardly into contact with the filter (FIG. 7).

Figure 5:
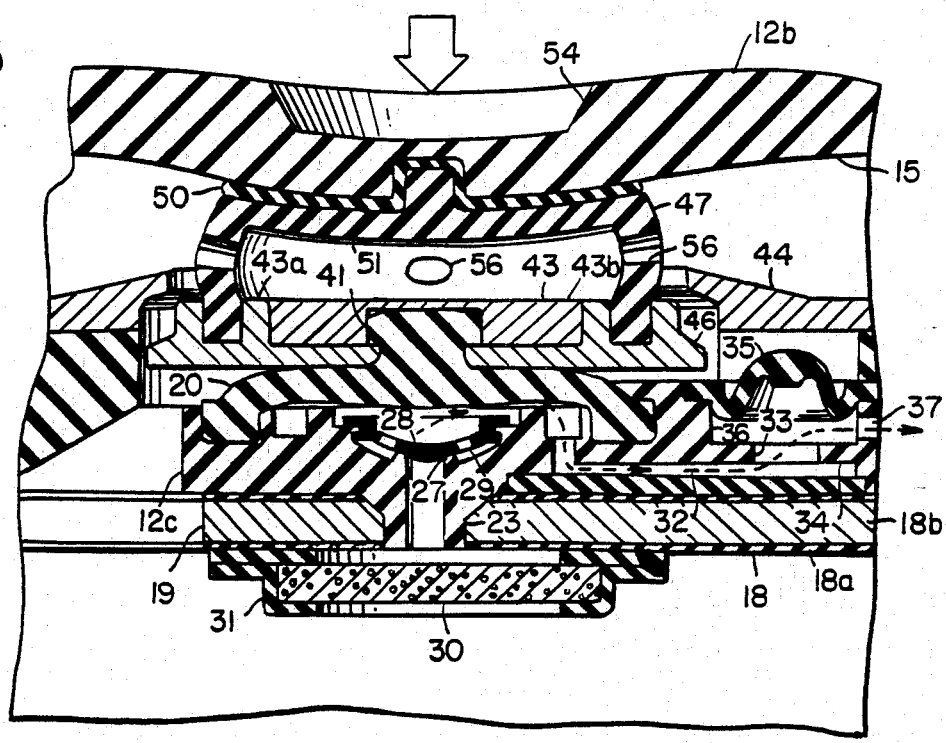
FIG. 5 is a fragmentary sectional view similar to FIG. 4 but illustrating the condition of the device during a pumping step.

A second passage 32 also communicates with the chamber 26 of the pump and leads radially away from the pump through the inner section 12c of the top wall. The second passage 32 is parallel and in close proximity to rigid support plate 18 and communicates at its opposite end with a valve opening 33 defined by an annular flexible lip 34 that is preferably formed integrally with section 12c of the top wall. The lip defines a valve seat and the opening 33 is normally closed by a cup-shaped elastomeric valve member 35 mounted within cylindrical chamber 36. In its normal undeformed state, valve member 35 engages lip 34 to maintain the valve in closed condition; however, as shown in FIG. 5, the valve member is capable of being deformed upwardly into unseated condition to allow fluid flow from secondary passage 32 and opening 33 into chamber 36 and then into outlet passage 37. The outlet passage leads to outlet port 38 which in turn communicates with the lumen of a catheter 39. A tapered ferrule or connector 40 is secured to the casing 11 and supports the catheter at its point of exit from the casing.

All of the elements so far described, except for filter disc 30 and the core 18b of support plate 18, are composed of soft, deformable material. Silicone rubber of the same formulation or different formulations may be used for all of such resilient elements which, as already indicated, are secured together by any suitable adhesive to provide the assembly illustrated in the drawings.

The dome-shaped pump housing 20 has an upstanding stem portion 41 that is anchored to a rigid disc 43 formed of polycarbonate or any other suitable material having sufficient strength, hardness, and rigidity to resist needle penetration. In the illustration given, the disc 43 is formed in two sections 43a and 43b to facilitate assembly, or subassembly, with pump housing 20; however, it is to be understood that if desired the rigid disc 43 may instead be formed in one piece.

Figure 4:
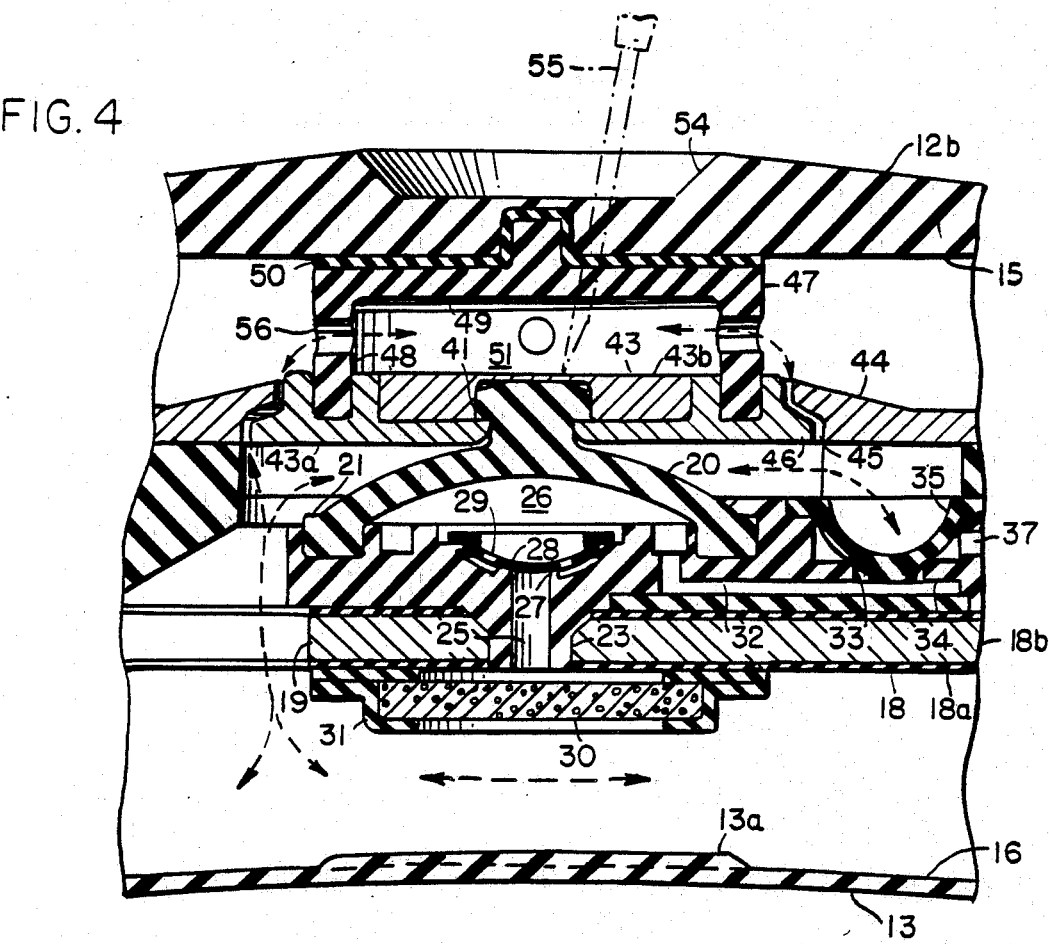
FIG. 4 is a still further enlarged vertical longitudinal sectional view showing the filling port, needle guard, and pump assembly.

The disc 43 is surrounded by an annular plate 44 that is also formed of rigid material, preferably the same material as disc 43. The periphery of the annular plate is locked in place between the central section 12b and the inner section 12c of upper wall 12. As shown in FIGS. 3 and 4, the opposing edges or side surfaces of the disc 43 and annular plate 44 are spaced apart to provide flow passages 45 that maintain the portions of the upper chamber above and below the disc and annular plate in pressure-equalizing flow relation. A rim 46 of the disc 43 projects outwardly and is engagable with the annular plate 44 to limit the extent of upward movement of the disc and, if desired, the rim may be serrated or discontinuous to insure that passages 45 remain open at all times.

Above disc 43 is an inverted cup-shaped septum 47 having an apertured side wall 48 and, when fully assembled, a planar end wall 49. The lower periphery of the side wall 48 is secured within an annular channel provided in rigid disc 43. The septum is formed of an elastomer such as silicone rubber and is secured to the underside of the central section 12b of the casing's top wall 12 by means of an adhesive attachment layer 50.

Figure 8:
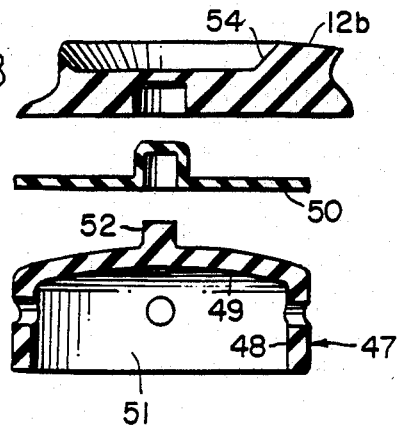
FIG. 8 is an exploded sectional view illustrating the deformable septum and associated parts prior to assembly.
Figure 9:
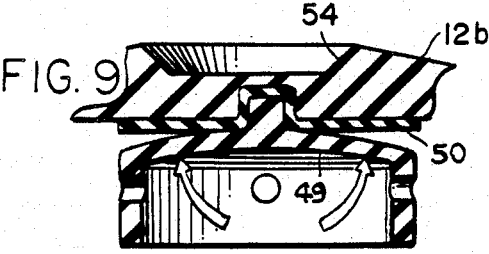
FIG. 9 is a sectional view illustrating the parts of FIG. 8 in partially assembled condition.

Of particular importance is the fact that end wall 49 of the elastomeric septum is spaced well above disc 43 to define a medicament-receiving chamber 51. Also, while shown in the assembly drawings to be of generally planar configuration (except for locating protuberance 52), the end wall in an untensioned state is dome shaped. As shown in FIG. 8, in the absence of distorting forces the convex end wall 49 curves upwardly and inwardly so that when flattened and adhesively secured to the planar undersurface of the casing's top wall section 12b, the end wall 49 will have its upper surface portion in a compressed state and will be maintained in that compressed state by adhesive layer or pad 50. It has been found that such limited compression of the upper stratum of end wall 49 greatly enhances the self-sealing properties of the septum upon withdrawal of an injection needle.

Ideally, the upper surface of the central section 12b of casing's top wall 12 is provided with an indentation 54 of circular outline. The indentation identifies the target site for both pump actuation and fluid injection and helps a user locate such site by touch even when the fluid delivery device is implanted. When fluid is to be supplied to the reservoir, the needle 55 of a syringe is simply inserted into the casing through the indented zone of the top wall until the tip of the needle engages (FIG. 4). Discharge of fluid from the syringe flows outwardly through openings 56 in the side wall of septum 47. Since the upper and lower chambers of the reservoir are in communication, such fluid enters the space above the dome-shaped pump housing 20 and above outlet valve member 35, and is free to pass into the lower chamber through opening 19. Upon removal of needle 55, the compressed end wall 49 of the septum 47 then closes and reseals the reservoir.

Figure 6:
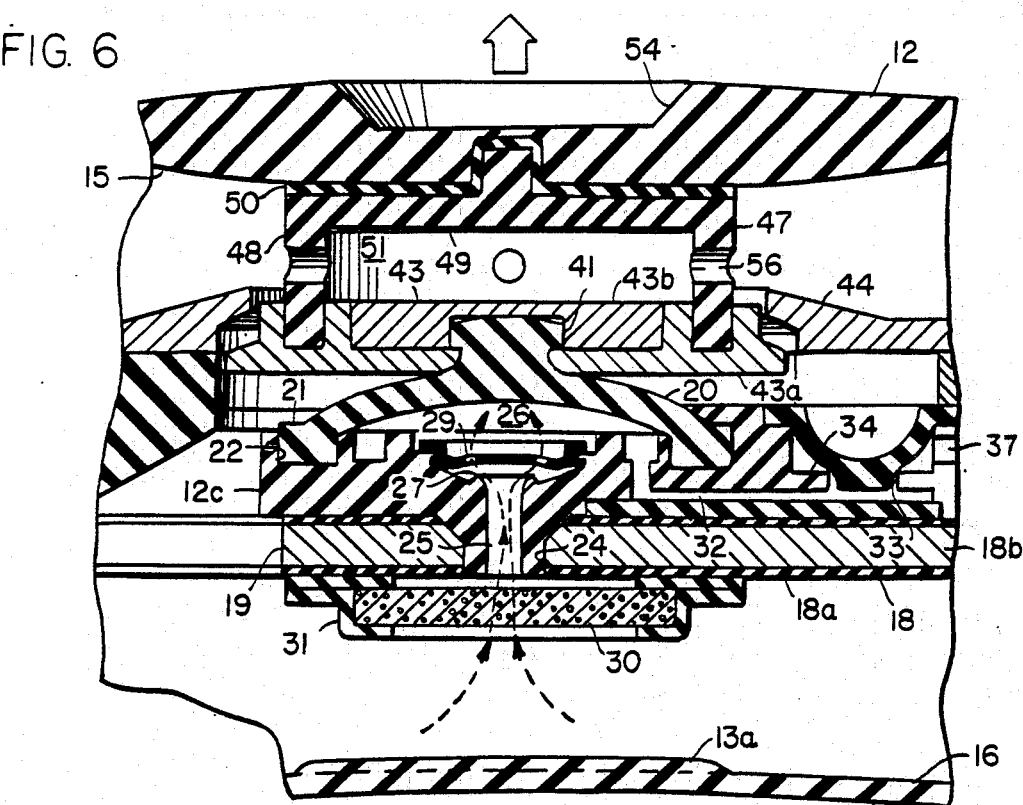
FIG. 6 is a similar fragmentary sectional view showing the parts during a recovery step in which the pump cavity is being refilled.

The same target zone, as defined by indentation 54, is used for finger actuation of the pump mechanism. Depression of the top wall 12 in the area of indentation 54, as depicted in FIG. 5, drives the septum 47 and rigid disc 43 downwardly, deforming pump housing 20 and substantially exhausting pump cavity 26. Fluid in the pump cavity is driven outwardly into second passage 32 with the pressure increase beneath outlet valve 35 causing the outlet valve to flex upwardly into open position. An aliquot of fluid substantially equal to the volume of pump chamber or cavity 26 (when the pump housing is undeformed) is therefore discharged into the outlet passage 37 and through outlet port 38. When finger pressure is removed, the top wall returns to its original position largely because of the recovery forces exerted by the dome-shaped pump housing 20 and the flexible top wall portion 12b. As the pump cavity 26 expands, the pressure differential causes the membrane valve member 28 to lift away from its seat 27, allowing fluid from the lower chamber 16 of the reservoir to enter the pump cavity 26 through the first passage 25 and openings 29 in the membrane (FIG. 6). Once the pump cavity is filled and pressure is equalized, the inlet valve member 28 closes and the parts again assume the relationships depicted in FIGS. 3 and 4.

Since the upper and lower chambers of the reservoir are in open communication at all times, deformations of the resilient casing 11 produced by body movement or other causes do not result in unintentional delivery of medicament to the patient. For example, should patient movement cause compression of the device and subsequent upward flexure of bottom wall 13 from the position shown in FIG. 4, fluid displaced from lower chamber 16 is free to enter the upper chamber of the reservoir, including the area directly above outlet valve member 35. The outlet valve will therefore remain closed despite the deformation of the casing because pressure will be equal on both sides of outlet valve 35. The double-headed arrows in FIG. 4 are intended to indicate the reversibility of movement of fluid throughout the upper and lower chambers of the reservoir that results in pressure equalization.

It will be observed from FIGS. 1 and 2 that casing 11 is of distinctive configuration, being of flattened pear shape with an enlarged body portion 70 and a reduced lateral portion 71. The target zone defined by depression 54 is generally centrally located in that portion of the casing's upper wall 12 that covers body portion 70, and a port 72, similar in appearance to depression 54, is provided in the upper wall portion that covers the casing's reduced lateral portion 71. Port 72 defines the target zone for a bolus injection site.

Since the lateral portion 71 of the casing is substantially narrower than body portion 70 and since the top surface of lateral portion 71 is stepped well below the outer top surface of body portion 70, a user may by tactile investigation readily distinguish the two portions of the casing and locate injection port 72 when the direct injection of a bolus of medicament is indicated. The laterally-spaced relation between the two sites contributes to the low profile of the device and, because of the substantial spacing between those sites, a user may readily distinguish one from the other and direct a needle of a syringe into the intended target zone.

The bolus injection port subassembly includes a rigid, cylindrical, open-ended, sleeve 73 mounted in a recess 74 formed in top wall 12 of the casing (FIG. 10). Like the core of the rigid support plate 18, sleeve 73 is advantageously formed of polycarbonate, although any of a variety of other materials having similar properties may be used. The frusto-conical surface defining port 72, in addition to defining the target zone for bolus injection, provides a hard and smooth deflecting surface for directing a needle into the cylindrical body or sleeve. A rigid filter 76 is secured within sleeve 73 at its lower end and, as shown in the drawings, is spaced directly above outlet passage 37. The filter may be formed of any suitable rigid, porous material and may be identical in composition and construction to the metal filter disc 30 at the entrance to inlet passage 25.

A membrane 77 formed of silicone rubber or other suitable elastomeric material is mounted within sleeve 73 at the upper end thereof, directly below frusto-conical surface 72. A spacer ring 78 disposed between filter 76 and membrane 77 completes the subassembly and maintains the membrane and filter in spaced relation with a bolus receiving chamber 79 disposed therebetween. The membrane 77 is of generally cylindrical shape when undeformed and uncompressed but, when mounted in sleeve 73, the membrane is in a state of radial compression that causes a slight upward and downward bowing or bulging of its upper and lower surfaces (FIG. 10). Such radial compression enhances the self-sealing properties of the membrane following withdrawal of an injection needle.

Use of the bolus injection site takes advantage of the implanted condition of the fluid delivery device 10 while at the same time bypasses the pumping mechanism of that device to permit direct delivery of a medicament to the outlet port 38. As shown in FIG. 10, a syringe needle 75 is inserted through membrane 77 and into chamber 79 with the extent of such insertion being controlled by the rigid protective filter 76. Medicament is injected into the chamber and passes through the filter directly into outlet passage 37 leading to outlet port 38 and catheter 39. Some backup of fluid may occur, as indicated by the arrows extending to the left in FIG. 10. While the pressure increase within the outlet passage 37 may cause outlet valve 35 to lift from its seat (FIG. 10), reverse flow is limited by membrane inlet valve member 28. More specifically, pressure increase within the chamber 26 of pump housing 20 forces the dish-shaped membrane valve member 28 downwardly into even tighter engagement with its valve seat 27, thereby preventing the reverse flow of fluid downwardly through inlet passage 25 and into the lower chamber of the reservoir.

The embodiment depicted in FIGS. 12 and 13 is identical in construction and operation to the one already described except that a protective grid member 80 is disposed within the inlet passage 25. The insert member is provided with a plurality of ribs 81 defining longitudinal flow passages 82 therebetween. When mounted within inlet passage 25, the insert member has its upper end disposed just slightly below valve seat 27. If desired, the lower end of the insert may be braced against rigid inlet filter disc 30 (FIG. 12). The thin membrane filter member 28 is therefore protected against substantial deformation and possible rupture should substantial back pressure develop during bolus injection. The inlet valve thus performs dual functions. It serves as a check valve during a pumping operation when top wall 12 is depressed in target zone 54 to deliver a metered amount of medicament contained in reservoir 17, and it also functions as a safety valve to limit reverse flow of fluid in the system during bolus injection.

While in the foregoing, an embodiment of the invention has been disclosed in considerable detail for purposes of illustration, it will be understood by those skilled in the art that many of these details may be varied without departing from the spirit and scope of the invention.

We claim:

1. An implantable, finger-pressure-activated device for dispensing metered amounts of fluid to a patient, comprising a casing formed of soft deformable polymeric material having a top wall and a bottom wall defining a fluid reservoir with an outlet port; pumping means within said casing comprising a compressible pump housing having a pumping chamber; said casing including an enlarged body portion and a reduced lateral portion; said top wall of said body portion having a central target zone for finger pressure activation of said pump when said target zone is depressed; and said reduced lateral portion having a bolus injection chamber communicating with said outlet port; said top wall of said reduced lateral portion having a bolus injection port adjacent said bolus injection chamber with said bolus injection port separated from said chamber by a needle-piercable self-sealing elastomeric membrane; first passage-providing providing means being provided within said casing and defining an inlet passage extending from said reservoir to said pump chamber an annular valve seat at one end of said inlet passage facing said pump housing within said pump chamber; an elastomeric inlet valve member mounted within said pump chamber and normally engaging said valve seat to close said inlet passage; second passage-providing means defining an outlet passage extending from said pump chamber to said outlet port; said bolus-receiving chamber communicating with said outlet passage; whereby, medicament injected into said outlet passage through said bolus injection port is prevented from entering said inlet passage and said reservoir by said inlet valve member; and a grid member being mounted in said inlet valve passage; said grid member having a flow passages extending longitudinally therethrough and an end portion surrounded by said valve seat for engaging and bracing said elastomeric inlet valve member when back pressure develops in said pump chamber.

2. The device of claim 1 in which said inlet passage extends through a wall portion formed of elastomeric material; said wall portion engaging and being supported upon a rigid support plate disposed within said casing; and a rigid porous filter element secured to said support plate beneath said inlet passage; said grid extending through said inlet passage and being supported by said filter element.

* * * * *